United States Patent [19]

Fischell

[11] Patent Number: 4,559,931
[45] Date of Patent: Dec. 24, 1985

[54] MANUALLY ACTUATED FULLY IMPLANTABLE PENILE ERECTION DEVICE

[76] Inventor: Robert E. Fischell, 1027 McCeney Ave., Silver Spring, Md. 20901

[21] Appl. No.: 476,931

[22] Filed: Mar. 21, 1983

[51] Int. Cl.⁴ .............................................. A61F 5/00
[52] U.S. Cl. ................................................... 128/79
[58] Field of Search .................. 128/79, 1 R, 344; 3/1

[56] References Cited

U.S. PATENT DOCUMENTS

| | | | |
|---|---|---|---|
| 1,133,958 | 3/1915 | Henderson . | |
| 3,289,451 | 12/1966 | Koch et al. | 72/283 |
| 3,731,681 | 5/1973 | Blackshear et al. | 128/214 F |
| 3,832,996 | 9/1974 | Kalnberg | 128/79 |
| 3,853,122 | 12/1974 | Strauch et al. | 128/79 |
| 3,954,102 | 5/1976 | Buuck | 128/79 |
| 4,009,711 | 3/1977 | Uson | 128/79 |
| 4,151,840 | 5/1979 | Barrington | 128/79 |
| 4,193,397 | 3/1980 | Tucker et al. | 128/207.19 |
| 4,201,202 | 5/1980 | Finney et al. | 128/79 |
| 4,221,219 | 9/1980 | Tucker | 128/260 |
| 4,224,934 | 9/1980 | Scott et al. | 128/79 |
| 4,235,227 | 11/1980 | Yamanaka | 128/79 |
| 4,267,829 | 5/1981 | Burton et al. | 128/79 |
| 4,318,396 | 3/1982 | Finney | 128/79 |
| 4,342,308 | 8/1982 | Trick | 128/79 |
| 4,353,360 | 10/1982 | Finney et al. | 128/79 |
| 4,364,379 | 12/1982 | Finney | 128/79 |
| 4,369,771 | 1/1983 | Trick | 128/79 |
| 4,383,525 | 5/1983 | Scott et al. | 128/79 |
| 4,399,811 | 8/1983 | Finney et al. | 128/79 |
| 4,399,812 | 8/1983 | Whitehead | 128/79 |
| 4,407,278 | 10/1983 | Burton et al. | 128/79 |
| 4,424,807 | 1/1984 | Evans, Sr. | 128/79 |
| 4,437,457 | 3/1984 | Trick et al. | 128/DIG. 25 X |

OTHER PUBLICATIONS

F. B. Scott et al., *Urology,* Jul. 1973, pp. 80-82.

*Primary Examiner*—Stephen C. Pellegrino
*Attorney, Agent, or Firm*—Fleit, Jacobson, Cohn & Price

[57] ABSTRACT

Disclosed is a manually actuated, fully implantable, penile erection device. Two stiffener cylinders are adapted for implantation in the penis of the patient, and are in fluid communication with two remote fluid control chambers, an actuator chamber and a releaser chamber. This actuator chamber and the releaser chamber are adapted to be manipulated through the skin of the patient to control the fluid pressure in the system, and to control whether the stiffener cylinders are in their erect or in their flaccid states.

14 Claims, 9 Drawing Figures

MANUALLY ACTUATED FULLY IMPLANTABLE PENILE ERECTION DEVICE

BACKGROUND OF THE INVENTION

1. Field of the Invention

This invention relates to an improved, manually actuated, hydraulic device to provide a penile erection for human males who suffer the dysfunction of erectile impotence.

2. Description of the Prior Art

The normal male achieves an erection when a multitude of small blood vessels within a long cylindrical section on each side of the penis called the corposum cavernosum fills with blood as a result of an increase in the vessels' output resistance to blood flow. There are two such parallel cylinders in the penis (the plural being the corpora cavernosa) which simultaneously become engorged with blood thereby producing a penile erection. Unfortunately, there are 10 million men, in the United States alone, who are unable to achieve a penile erection.

There are many causes for impotency in the human male, both psychological and physiological. Among the physiological causes are: long term diabetes, damage to the spinal cord, multiple sclerosis, a surgical procedure in the lower abdomen that has caused nerve damage in the genital region, and advanced age. Such impotence often destroys the male's psychological well being, and often seriously disrupts or even causes the dissolutionment of otherwise fulfilling relationships. It therefore is not surprising to find that the patent art is replete with examples of artifical penile erection devices.

One of the earliest prosthetic devices whose object was to achieve a penile erection is described by Henderson in U.S. Pat. No. 1,133,958 (March 1915). This device suggests the use of an external truss to stiffen the penis by preventing the back-flow of blood. Since the truss is removable, it is a simple matter to obtain a normal flaccid state. However, the external truss mechanism also prevents in-flow of blood and, therefore, cannot provide the five conditions required of a normally erect penis; namely, during erection the penis should become longer, thicker, harder, stiffer, and have a generally upward angle.

Kalnberz, in U.S. Pat. No. 3,832,996 (September 1974), describes two stiff rods designed to be implanted in the corpora cavernosa to attain a penile erection. Although this system provides a longer, thicker, and stiffer erectile state, it does not provide a generally upward angle, and the flaccid state is no longer achievable.

An improved rod is described by Barrington in U.S. Pat. No. 4,151,840 (May 1979), which rod provides a longer, thicker, and stiffer erectile state. Furthermore, the device can be bent downwardly by hand to achieve the flaccid condition. However, in the flaccid condition, the penis is just as long and thick as in the erectile state; also, it is unnaturally stiff and hard.

A manually actuated fluid driven system is described by Strauch et al in U.S. Pat. No. 3,853,122 (December 1974). A serious difficulty in the Strauch et al system is that only a single inflatable, cylindrical stiffener is envisaged. To be effective, there must be stiffeners in each one of the two corpora cavernosa. If the stiffener is in only one corposum cavernosum, the erectile state of the penis will be badly distorted. Furthermore, with the Strauch device, fluid exits the region of the penis through a metering means not under the control of the implantee. The penis therefore could become flaccid too quickly, or could take an unreasonably long time to become flaccid, all depending upon the configuration of the metering means.

Buuck, in U.S. Pat. No. 3,954,102 (May 1976), describes a manually actuated, fluid driven, inflatable penile prothesis with two cylinders in the corpora cavernosa. The Buuck prosthesis achieves the erectile goals of a longer, thicker, harder, and stiffer penis with a generally (though not certainly physiologically sufficient) upward angle during erection, and also provides a physiologically normal flacid state. However, this device still has certain major shortcomings. For example, when the penis is in the erectile state, its upward angle may not reach that achieved in a normal male. Further, the pump and release valve are located in the scrotum, which is one of the body sites most disposed to post-operative discomfort and infection. The Buuck device requires multiple strokes of the pump within the scrotum to achieve an erection, which could require one or more minutes of pumping, especially if the patient is not particularly skilled in pumping a small bulb located within the scrotum. Furthermore, the release valve in the scrotum must be held for on the order of ten to fifteen seconds to return the penis to the flaccid state. Also, a comparatively large reservoir is required by Buuck because fluid cannot be added after implant without surgical intervention; and as a consequence of the large reservoir and small displacement pump used by Buuck, it is possible to permanently distend or even rupture the stiffener cylinders by excessive pumping. Additionally, because of the many separate pieces of tubing and other parts required by the Buuck device, it is necessary to fill and then assemble the many separate parts during the surgical implant; this is a time consuming (and therefore costly) procedure.

A further element of the prior art is U.S. Pat. No. 4,009,711 (March 1977) which issued to Uson, and which describes a non-distensible portion of a stiffener cylinder that is placed in the root of the corpus cavernosum, and a distensible portion that is located within the pendulous portion of the corpus cavernosum. Although there may be valid reasons to provide a structure such as that described by Uson, it is disadvantageous to have a considerable portion of the stiffener cylinder located within the root of the corpus cavernosum if it is not pliable and distensible. In this regard, some shortcomings of the Uson device are that the penis does not feel natural in the flaccid condition because there is a rigid object just beneath the skin at the base of there penis. Furthermore, the shape of the penis in the flaccid condition is not physiologically normal, nor is there stress relief provided for the elastomer stiffener cylinder during the flaccid state (which is most of the time) because the cylinder does not begin its downward curve while still supported within the root of the corpus cavernosum. Additionally, a greater extended length of the penis in the erectile state cannot be achieved because the cylinder does not begin its extension within the root of the corpus cavernosum.

SUMMARY OF THE PRESENT INVENTION

It is, therefore, highly desirable to provide a simple, safe, reliable and easy to operate implantable device whereby the impotent male can achieve a penile erection that is physiologically normal; i.e., the device should cause the penis to become longer, thicker, harder and stiffer, and to assume generally upward angle. It is further desirable to have the penis return to a normal, flaccid condition at all times other than during sexual activity. Ideally, these two physiologically normal operating characteristics should be achievable promptly on command of the individual in whom the device is implanted.

To this end, one object of the present invention is to provide a means for readily causing the penis to achieve an erectile state which is physiologically equivalent to that of the normal male. Specifically, an object is to provide a device whereby the penis becomes longer, thicker, harder and stiffer, and attains a proper upward angle.

Another object of the invention is to provide a penile erection device having a readily achieved and physiologically normal flaccid state.

Yet a further object is to provide a penile erection device wherein the erectile state can be achieved rapidly (in less than on the order of 3 seconds) by a single push of an actuator located just beneath the skin in the lower abdomen.

Still another object of the invention is to provide a device wherein the flaccid state can be achieved rapidly (in less than on the order of 3 seconds) by a single push of a releaser located just below the skin at the base of the penis.

A further object of the invention is to provide an effective, fully implantable device, wherein no part of the structure is located in the scrotum.

Another object of the present invention is to provide a device wherein the actuator is designed with limited capacity to deliver fluid so that two stiffener cylinders located in the corpora cavernosa cannot be overfilled.

Yet a further object of the invention is to provide a fully implantable penile erection device including means for post-operatively adjusting the fluid level within the device, without surgical intervention, for adjusting the erectile and flaccid states.

Still another object of the invention is to provide a device that is assembled and pre-filled prior to surgical implantation so that the time required for the surgical implant is reduced.

Yet a further object of the present invention is to provide a fully implantable penile erection device wherein bottom shells of the actuator and the releaser are provided with at least one concave surface which improves implant positional stability.

These and other objects of the invention, as well as many of the attendent advantages thereof, will become more readily apparent when reference is made to the following description, taken in conjuction with the accompanying drawings.

DETAILED DESCRIPTION OF THE DRAWINGS

Figure 1:
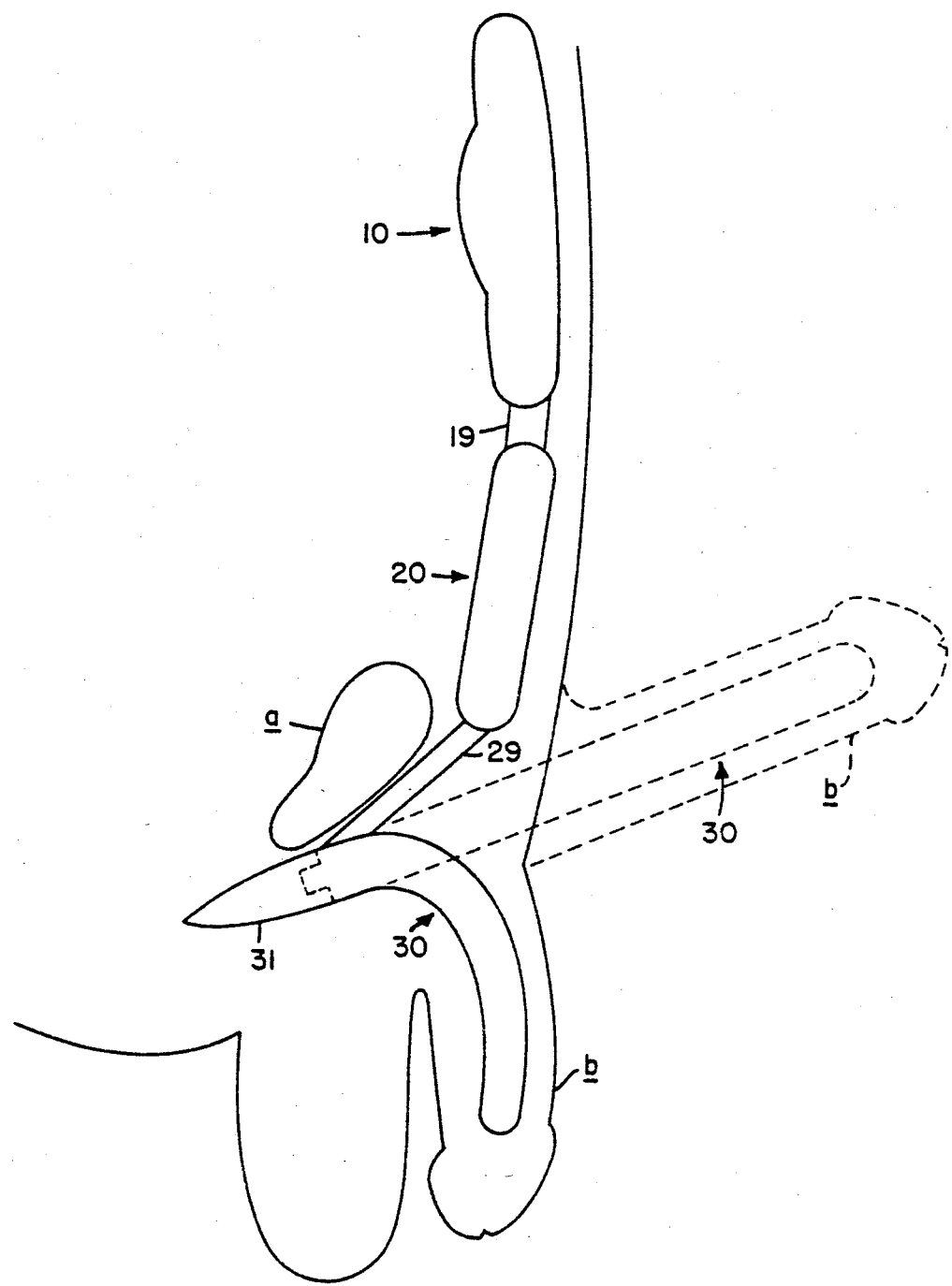
FIG. 1 is a side view of the implantable penile erection device, in its fully implanted position, showing the various elements of the device and showing the penis in both the flaccid and the erectile states.

FIG. 1 shows the present invention as it would be implanted within a human male. An actuator, illustrated at 10, is joined to a releaser 20 by connecting tubing 19. The connecting tubing 19 is preferably formed from an elastomer such as medical grade silicon rubber. The releaser 20 has two outlets, each one of which is connected to a respective stiffener cylinder 30 (only one of which can be seen). Each stiffener cylinder 30 has a rigid portion, or root extender, 31. As can be seen, a stiffener connecting tubing 29 places the releaser 20 in fluid communication with each stiffener cylinder 30, and is implanted just anterior to the pubic bone a.

In FIG. 1, the penis is shown at b, with its flaccid condition being in solid lines and its erect condition being in dashed lines. Similarly, the flaccid state of the stiffener cylinder 30 is shown in solid lines, while the erect state is shown in dashed lines. As noted above, two side-by-side stiffener cylinders 30 are implanted in the corpora cavernosa, although only one is illustrated in FIG. 1.

Figure 2:
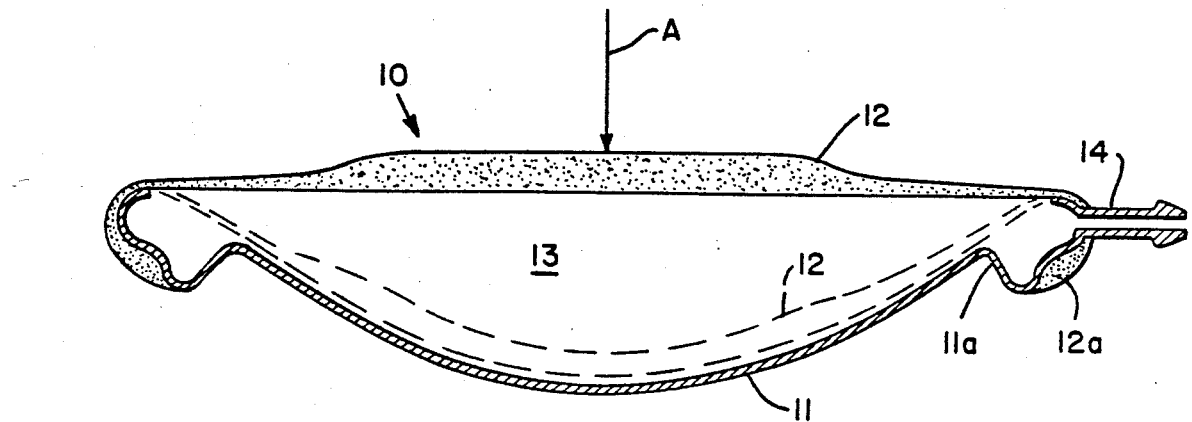
FIG. 2 is a cross-sectional view of the actuator.

FIG. 2 is a cross-sectional view of the actuator 10. A thin bottom shell 11 is fabricated from a biocompatible metal such as titanium, and is joined at its uppermost portion to a biocompatible elastomer diaphragm/septum 12. The elastomer might typically be medical grade silicon rubber. Shell 11 is connected to diaphragm/septum 12 such that the junction between the shell and the elastomer diaphragm/septum defines an increased thickness or bead 12a which holds the diaphragm/septum 12 securely to the shell 11.

The shape of the shell 11 includes a concave surface 11a that provides an increased bottom surface area for the actuator 10. When implanted in the human body, the actuator 10 becomes "walled off" by tough connective tissue generated by the body, that holds the actuator securely in place. The concave surface 11a increases the bottom surface area of the actuator 10, and therefore increases the available contact area between the connective tissue and the implanted device, thus tending to hold the implant more securely. Furthermore, when the actuator 10 is manually pushed at its center (shown by arrow A), i.e., by finger pressure through the skin, the concave shape defined by the surface 11a provides a stabilizing force that tends to prevent sidewise dislodgement of the actuator 10.

When manually actuated, the diaphragm/septum 12 can be depressed to the position shown in dashed lines in FIG. 2. The relaxed position of diaphragm/septum 12, shown in solid lines, corresponds to the flaccid state of the penis; the actuation position of the diaphragm/septum 12 shown in dashed lines, corresponds to the erectile state of the penis. Because the bottom shell 11 limits the travel of the diaphragm/septum 12, the stiffener cylinders 30 cannot be overfilled. This prevents plastic deformation and rupture of the stiffener cylinders 30, a risk of the designs having large reservoirs and small, multi-stroke pumping means.

As the diaphragm/septum 12 is manually depressed through the skin (in the direction of arrow A) toward its position corresponding to the erectile state, an incompressible, sterile, radio-opaque, isotonic fluid 13 (such as that used for cystographic studies) is forced out of the actuator 10 through the outlet tube 14 and connecting tubing 19, and into the releaser 20 (FIG. 1). The force required to so depress the diaphragm/septum 12 is on the order of 10 pounds, with the diaphragm/septum typically being on the order of 3 inches in diameter and 0.1 inch thick at its thickest point.

Figure 3:
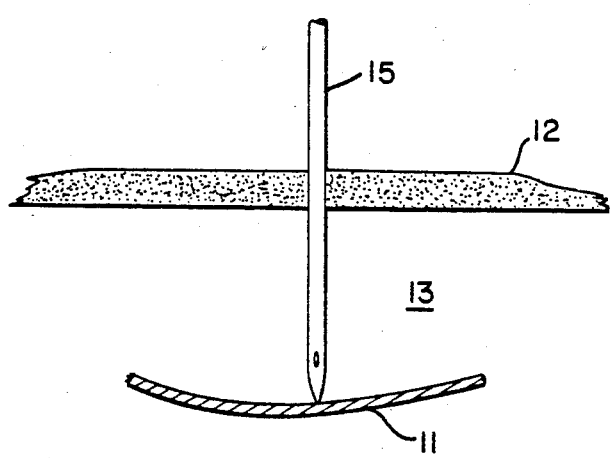
FIG. 3 illustrates a method of using a non-coring hypodermic needle to penetrate the diaphragm/septum of the actuator for post-operatively adjusting fluid volume.

Diaphragm/septum 12 also serves as a self-sealing septum through which fluid can be added or removed from the device. In this regard, FIG. 3 shows a section at the center of the diaphragm/septum 12 of the actuator 10 which is pierced by a non-coring (Whitacre point) hypodermic 15. The needle 15, connected to a hypodermic syringe (not shown), can be readily used to add or remove fluid 13 from the actuator, and, therefore, from the entire implant system. This can be readily performed without surgical intervention. Fluid may be added to provide a firmer erectile state, or may be removed to soften the flaccid state, as desired.

The volume of fluid expelled from the actuator 10 by a single thrust of the diaphram/septum 12 is designed to be substantially equal to the volume of fluid needed in the stiffener cylinders 30 to bring the penis from its flaccid to its erectile state. This volume is on the order of 12 ml for a penis of typical size.

Figure 4:
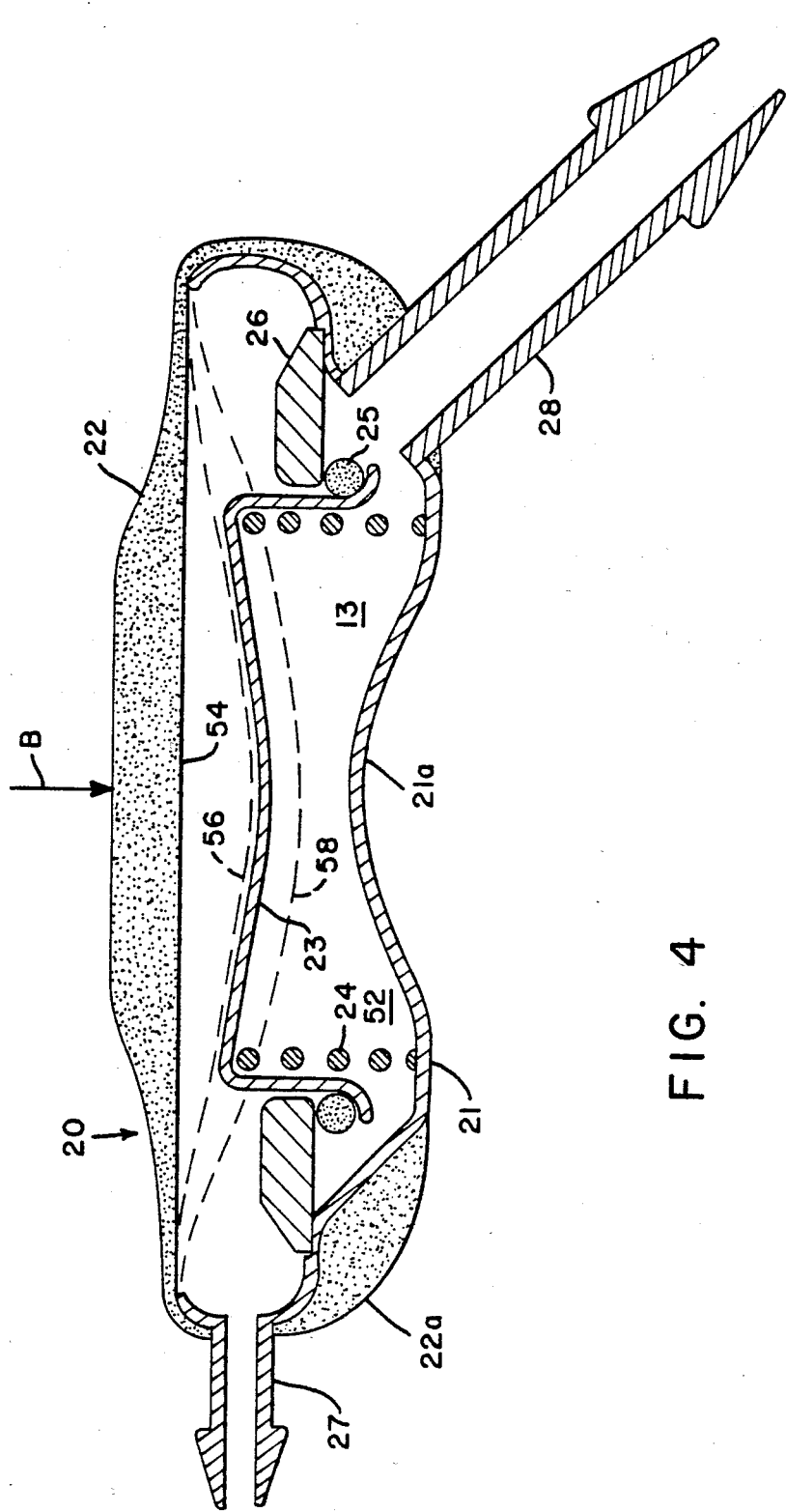
FIG. 4 is a cross-sectional view of the releaser.

As illustrated in greater detail in FIG. 4, the releaser 20 is of similar design to the actuator 10 in that it has a bottom metal shell 21 and an elastomer diaphragm 22 that is firmly fixed to the shell 21 by a bead 22a. The shell 21 has a concave surface 21a for the purpose of improving implant positional stability, as was previously explained with respect to concave surface 11a of the actuator shell 11.

The diaphragm 22 typically is of the same medical grade silicon rubber as the actuator diaphragm/septem 12. Although it is technically achievable, the diaphragm 22 does not serve the additional function of a septum, since all fluid interchange is readily accomplished by means of the diaphragm/septum 12 of the actuator 10.

When the diaphragm/septum 12 is depressed in the direction of arrow A (FIG. 2), fluid 13 flows into the upper chamber 50 of the releaser 20. Then, when sufficient pressure is generated by the ingress of fluid 13, a valve poppet 23 opens; that is, poppet 23 moves downwardly against the force of a poppet helical spring 24 (having a spring constant on the order of 5 lbs/in). Such poppet opening permits fluid 13 to flow past an "O"-ring 25, and into a lower chamber 52 of the releaser 20. Fluid 13 then flows through the outlet tubes 28 of releaser 20, through the stiffener connecting tubings 29 (FIG. 1), and into the stiffener cylinders 30, resulting in the stiffener cylinders 30 attaining the erectile position shown in dashed lines in FIG. 1. As noted previously, there are two stiffener cylinders 30, and each associates with an an outlet tube 28 and a segment of connecting tubing 29.

When the diaphragm/septum 12 of the actuator 10 is released after depression in the direction of arrow A (it may have reached the full extent of its travel against the wall of shell 11, or it may have stopped at an intermediate position), the poppet 23 urges "O"-ring 25 against valve seat 26, because of the force from the spring 24, thus preventing the return of fluid 13 back into the actuator 10 from the respective stiffener cylinders 30 and from the releaser 20. The surface of the valve seat 26 in contact with the "O"-ring 25 should be flat and polished to a mirror finish to assure a good seal and thus to prevent back-flow of fluid 13 when it is desired to maintain the erectile state.

With the system is in the erectile state, the fluid in the actuator 10, and the fluid in the upper chamber 50 of the releaser 20, experience a negative gauge pressure (on the order of $-5$ psig). The fluid in the lower chamber 52 of the releaser 20, and the fluid in the stiffener cylinders 30, on the other hand, experience a positive gauge pressure (on the order of $+5$ psig). The resulting difference in fluid pressure across the comparatively large area of the valve poppet 23 causes an additional force on the poppet 23 that tends to further seal the "O"-ring 25 against the valve seat 26. If the area of "O"-ring 25 is A, the difference in pressure across the valve poppet 23 is p, and the closing force of the helical spring 24 is f, then the total force tending to keep the poppet 23 closed is given by $F = f + (p)A$. If the mass of the poppet 23 plus "O"-ring 25 is given by m, then the acceleration required to open the poppet must exceed a value a given by the equation $a = F/m$. Since the poppet 23 and "O"-ring 25 can be made with very little mass, and since the force F can be several pounds, even the most violent motions occurring during the erectile state will not be able to unintentionally open the poppet 23.

When there is a negative gauge pressure in the upper chamber 50 of the releaser 20, the bottom 54 of the diaphragm 22 moves inwardly and adopts the position shown by dashed line 56 in FIG. 4. The tension in the diaphragm 22 and its thickness and elastomer stiffness (i.e., durometer) are controlled so that the diaphragm 22 does not touch the top of the poppet 23 during the erectile state. Still, however, when the diaphragm 22 is in the position shown at 56, negative pressure in upper chamber 50 further ensures that inadvertent return to the flacid state is prevented. The diaphragm 22 is undeformed during the flaccid state, and adopts the repose position shown in solid lines in FIG. 4. The diaphragm 22 can be constructed of 50 durometer rubber, and typically is on the order of 2 inches in diameter and 0.1 inch thick at its thickest point. Poppet 23 typically is on the order of 1 inch in diameter.

To return the penis to its flaccid from its erectile state, the skin above the site where the releaser 20 is implanted is pressed in the direction of arrow B (FIG. 4) so that the bottom surface 54 of the diaphragm 22 reaches the position shown by dashed line 58. The poppet 23, including the "O" ring 25, is then urged away from the valve seat 26, thereby allowing fluid 13 to flow back from the stiffener cylinders 30 through the releaser 20, and into the actuator 10, thereby equalizing the pressure in the various chambers of the system.

Returning to FIG. 2, it can be seen that the energy stored in the diaphragm/septum 12 of the actuator 10, when the diaphragm/septum is manually depressed to the dashed line position, provides a negative pressure in the actuator 10 and thus provides the major portion of the energy required to pull the fluid 13 back into the actuator 10 when poppet 23 so permits. Some energy also is stored in the elastic deformation of the stiffener cylinders 30 during the erectile state, which energy is given up in returning the fluid 13 through the releaser 20 to the actuator 10. Furthermore, the force and energy required to return the fluid 13 to the actuator 10 can be enhanced by manually squeezing the penis while simulatenously exerting a force in the direction of arrow B onto the diaphragm 22 of the releaser 20. Indeed, the actuator can even be "overfilled" so that the fluid 13 resides therein at a positive pressure; in this way, manually actuating the releaser 20 causes some fluid to be delivered back to the stiffener cylinders 30 without manually pressing the diaphragm/septum 12 of the actuator 10.

Figure 5:
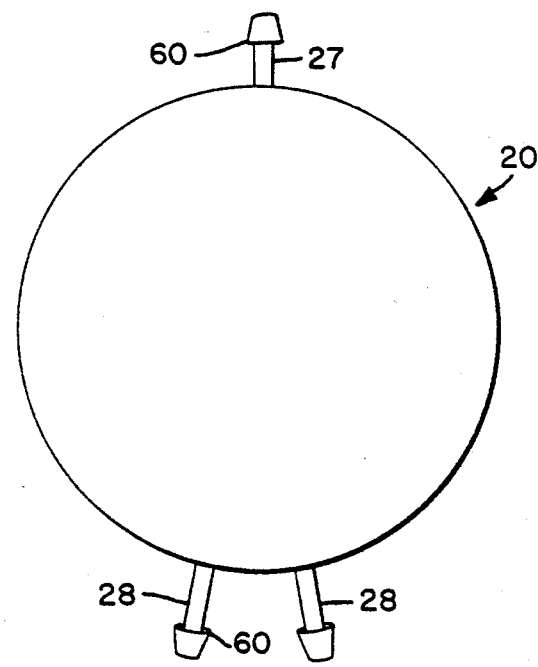
FIG. 5 is a plan view of the releaser.

FIG. 5 shows a top plan view of the releaser 20. As can be seen, the body of the releaser 20 is disc shaped, and is provided with an inlet tube 27 and two outlet tubes 28. Each inlet and outlet tube has a shoulder section 60 that is designed to retain the silicon rubber connecting tubing 19 which joins the releaser 20 to the actuator 10, and the silicon rubber connecting tubing 29 that is integral with and connects the stiffener cylinders 30 to the releaser 20.

The spring 24 of releaser 20 preferably is made of a titanium alloy such as 90% titanium, 6% aluminum and 4% vanadium. To eliminate the possibility of electrochemical corrosion between the various metal parts of the releaser 20 (since the fluid 13 likely is an electrolyte) all the metal parts (21, 23, 24, 26, 27 and 28) of the releaser 20 preferably are fabricated from the same titanium alloy.

Figure 6:
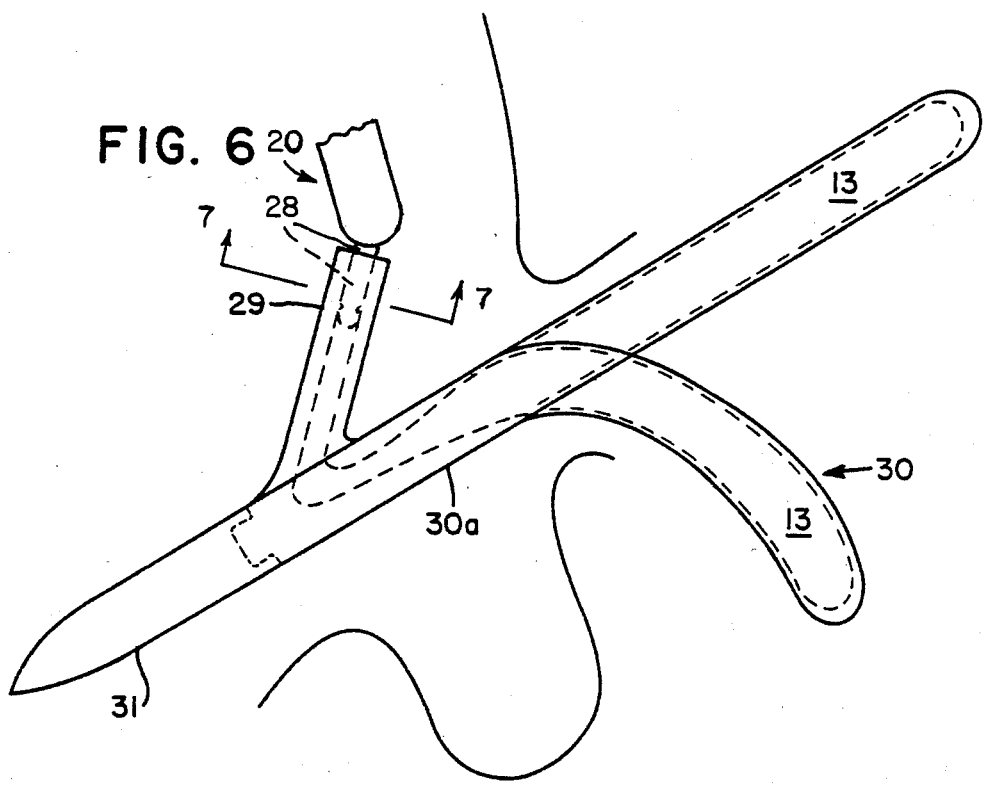
FIG. 6 shows he details of a stiffener cylinder, both in its flaccid and erectile states.

Referring to FIG. 6, a stiffener cylinder 30 can be seen in its flaccid state and in its erectile state. Fluid 13 enters the two stiffener cylinders 30 through the respective segments of connecting tubing 29. A root extender 31 is integral with or attached to the root 30a of each stiffener cylinder 30. The root 30a of the stiffener cylinder 30 is flexible, so that there is no hard object felt under the skin, and so that there is a more natural downward curve of the penis during its flaccid state. Also, root 30a provides a region of stress relief of the elastomer material where it is still within the root of the corpus cavernosum, and provides some elastic extension of the root 30a of the stiffener cylinder 30 within the root of the corpus cavernosum during the erectile state. As noted previously, the stiffener cylinders 30 contain the fluid 13 at approximately ambient pressure during the flaccid state, and at a higher pressure during the erectile state.

Figure 7:
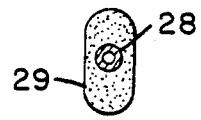
FIG. 7 is a cross-sectional view of the tubing that connects the releaser to a stiffener cylinder, taken along the line 7—7 of FIG. 6.

FIG. 7 shows a cross section of the stiffener cylinder connecting tubing 29, including the outlet tube 28 of the releaser 20. As can be seen, there is increased thickness of the elastomer material in the vertical dimension of connecting tubing 29. This provides additional stiffness in the vertical direction, which is important if a physiologically normal upward angle of the penis is to be achieved during the erectile state (See FIG. 1). The releaser 20 will be firmly encased in connective tissue, and also will be firmly attached to the stiffener cylinders 30 by means of the respective outlet tubes 28 and connecting tubing 29. This structuring provides an additional foundation for the stiffener cylinders 30, which, in turn, provides a torque so that the penis achieves the desired physiologically normal, upward angle during the erectile state.

The releaser outlet tube 28 is on the order of 1 inch in length so that it projects only about one-half the distance into the connecting tubing 29. Thus the connecting tubing 29 is somewhat flexible in the region where it is free from the effects of the outlet tube 28. As a result of this design, and owing to the decreased horizontal dimension of the connecting tubing 29, the stiffener cylinders 30 are able to readily enter corposa cavernosa of various separations without undue bending of the stiffener cylinders themselves as they enter each such corpus cavernosum. That is, the stiffener cylinders 30 have a greater freedom of motion in the horizontal direction as compared to the vertical direction.

Figure 8:
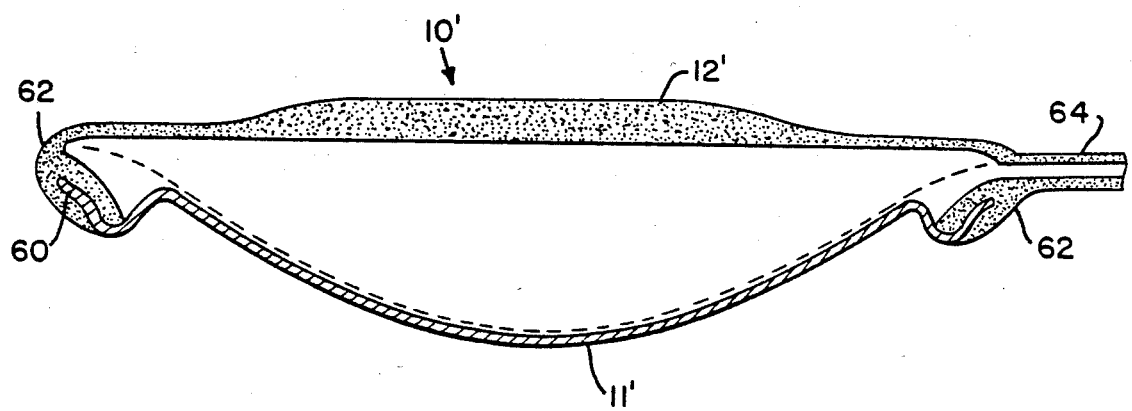
FIG. 8 is a cross-sectional view similar to that of FIG. 2, showing an alternate embodiment of the actuator.

With reference, now, to FIG. 8, a second embodiment of the actuator, designated 10', will be described. Actuator 10' differs from the actuator 10 described when reference was made to FIG. 2, in two major respects. First, in actuator 10', shell 11' does not wrap around to the upper portion of the actuator, but terminates at 60. Then, to join the diaphragm/septum 12' to the shell 11', the diaphragm/septum covers the edge 60 of shell 11' as shown at 62. It also should be noted that the silicon rubber at 62 protrudes, in a radial direction, farther than does the edge 60 of shell 11'. In this manner, the circumferential periphery of the actuator 10' is more pliable and therefore is less discernible if the skin above the implant site is touched.

The second major difference of actuator 10' is that the outlet tube, illustrated at 64, is fabricated from silicone rubber and is integral with the diaphragm/septum 12'. This unitary construction results in a more pliable actuator, and a less costly and less complicated construction.

Figure 9:
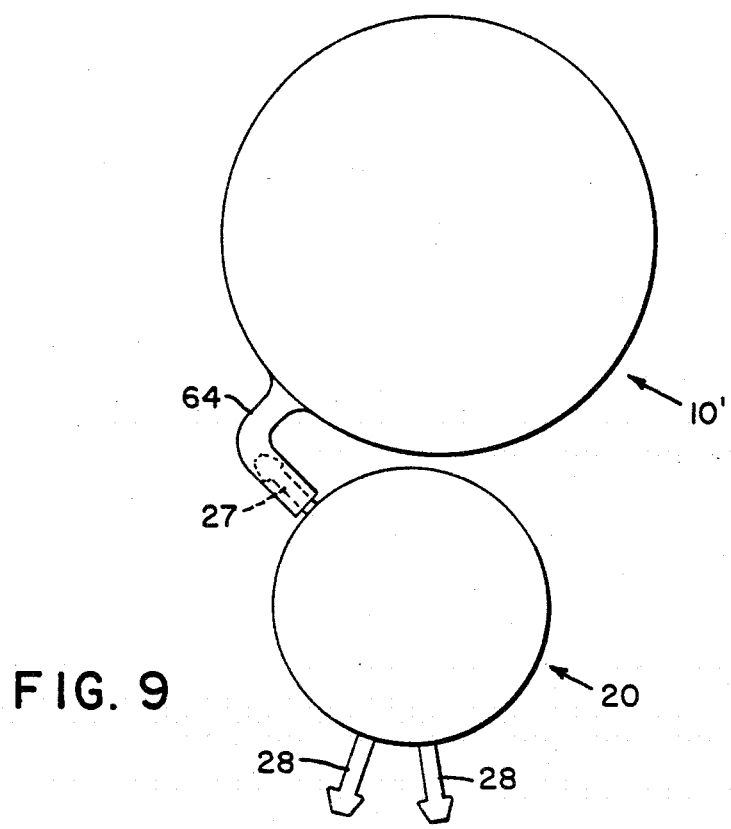
FIG. 9 is an illustration showing an alternate arrangement for connecting the actuator to the releaser.

In FIG. 9, there can be seen an actuator 10' connected to a releaser 20. While it is possible to connect the two components so that a straight line between the center and the outlet tube 64 of actuator 10' passes through the center of releaser 20, the components are shown to be connected so that there is an approximate 90° displacement angle therebetween. In this manner, more relative motion between the actuator 10' and the releaser 20 is permitted, thus minimizing component stress. In all other respects, the system is configured as is illustrated in FIG. 1.

Finally, with respect to the stiffener cylinders 30, many of the known designs can be utilized in the system set forth herein. It is essential only that the cylinders 30 be soft and pliable at one given fluid pressure (atmospheric) in the flaccid state and be erect and expanded on the order of 20 percent in volume and 5% in length in the erectile state at a higher fluid pressure of on the order of +5 psig. This can be accomplished with a single central fluid chamber or with a multiplicity of parallel or intermingling fluid chambers.

Various other modifications, adaptations and alternative designs are, of course, possible in light of the above teachings. Therefore, it should be understood at this time that within the scope of the appended claims, the invention may be practiced otherwise than as specifically described herein.

What is claimed is:

1. A penile erection device that is fully implantable in a patient and that includes stiffener means adapted for implantation in the body of the penis which adopts an erect state when pressurized to a first pressure and which adopts a flaccid state when pressurized to a lower second pressure; actuator means including an elastomeric surface adapted for depression from external to the patient to raise the pressure of a fluid in said stiffener means from said second to said first pressure; connecting means for establishing a fluid path between said stiffener means and said actuator means for transmitting fluid between said actuator means and said stiffener means; releaser means in the path of said connecting means, including a valve, and adapted for direct manual actuation from external to the patient to act on the valve and lower the pressure in said stiffener means from said first to said second pressure; the depressed elastomeric surface of said actuator means and the valve of said releaser means cooperating with said stiffener means so that when said stiffener means is in its erect state, a negative pressure is developed in a portion of said releaser means, serving both to urge the valve of said releaser means into a position to maintain the erect state and to rapidly drop the pressure in the stiffener means from said first to said second pressure when the releaser means is manually actuated.

2. A rapid acting and safe penile erection device fully implantable in a patient, the device comprising, in combination, stiffener means adapted for implantation in the body of a penis, said stiffener means having a fluid chamber which, when pressurized with a maximum volume of fluid at a first and safe pressure, causes said stiffener means to become rigid, and which, when pressurized with a lesser volume of fluid at a lower second pressure, causes said stiffener means to become flaccid; fluid-filled actuator means in fluid communication with the fluid chamber of said stiffener means, adapted for actuation by a direct manual thrust from external to the patient, said actuator means having a maximum safe volume of fluid therein so that substantially a single manual thrust substantially empties the fluid from said actuator means and delivers substantially the same volume of fluid to said stiffener means and hence raises the pressure in said stiffener means from the second to the first pressure, and having a mechanical stop to limit the amount of fluid delivered from said actuator means to said stiffener means and hence to limit the pressure in said stiffener means to said first pressure; and releaser means in fluid communication with said stiffener means and said actuator means, for maintaining the fluid in said stiffener means at said first pressure and adapted for direct actuation from external to the patient, for releasing fluid from said stiffener means and thereby returning the pressure in said stiffener means from said first to said second pressure.

3. The penile erection device as in claim 2, wherein partial manual thrust to said actuator means results in preselection of rigidity in said stiffener means corresponding to any stiffener pressure between said first pressure and said lower second pressure.

4. The penile erection device as in claim 2, wherein said actuating means is disk-shaped.

5. The penile erection device as in claim 2, wherein said releaser means is disk-shaped.

6. The penile erection device as in claim 2, wherein the valve in said releaser means is a poppet valve and includes a spring for biasing said poppet valve toward a closed position, said poppet valve serving to maintain said first pressure in said stiffener means after said actuator is manually actuated and is in repose, and serving to lower the pressure in said stiffener means to said second pressure during the time when said releaser means is manually actuated.

7. The penile erection device as in claim 2, wherein said actuator includes a penetrable surface for adding fluid thereto.

8. The penile erection device as in claim 2, wherein the surface of said actuator adapted to reside nearest the skin of the patient is an elastomeric surface.

9. The penile erection device as in claim 2, wherein said releaser means includes an elastomeric surface adapted to reside nearest the skin of the patient and adapted to receive said direct manual thrust; and a valve surface spaced from said elastomeric surface for being moved by said elastomeric surface to act on the valve and lower the pressure in said stiffener means when actuated.

10. The penile erection device as in claim 2, wherein said actuator means includes a rigid base member on which is mounted said elastomeric surface.

11. The penile erection device as in claim 2, wherein said fluid-filled actuator means and said stiffener means cooperate in such manner that when said fluid pressurizes the chamber of said stiffener means to fast pressure, a negative pressure is developed between said actuator means and said releaser means so that the rigid state of said stiffener means is enhanced until actuation of said releaser means.

12. A method of implanting a penile erection device in a patient, which device includes an inflatable stiffener means adapted for implantation in the body of the penis which adopts an erect state when pressurized at a first pressure and which adopts a flaccid state when pressurized at a lower second pressure, an abdominal actuator means in fluid communication with said stiffener means and adapted for direct manual actuation from external to the patient to deliver fluid to said stiffener means and hence raise the pressure of a fluid in said stiffener means from said second to said first pressure, and an abdominal releaser means intermediate and in fluid communication with said stiffener means and said actuator means, adapted for direct manual actuation from external to the patient to lower the pressure in said stiffener means from said first to said second pressure, the method comprising the sequential steps of: preassembling said stiffener means, said actuator means and said releaser means, and charging the device with said fluid; and implanting the assembled penile erection device in the patient by introducing said stiffener means to the body of the penis, by introducing said actuator means to the abdomen of the patient, and by introducing said releaser means to the abdomen of the patient, all without disturbing the preassembled state of the penile erection device.

13. The method recited in claim 12, and further comprising the step of: filling the device with a predetermined quantity of said fluid intermediate the steps of preassembling and implanting.

14. A penile erection device fully implantable in a patient, the device comprising, in combination: stiffener means adapted for implantation in the body of a penis, said stiffener means being provided with a fluid chamber which, when pressurized with fluid at a predetermined first pressure, causes said stiffener means to become rigid; fluid-filled, substantially disc-shaped actuator means adapted for subcutaneous implantation in the patient and adapted for actuation by a single direct manual thrust from external to the patient, said actuator means being provided with a substantially radial outlet through which fluid exits when said actuator is actuated; connecting means for establishing a fluid path between said actuator means and said stiffener means, for transmitting said fluid to said stiffener means, thereby pressurizing the chamber of said stiffener means to said first pressure; and substantially disc-shaped releaser means separate from and intermediate said stiffener means and said actuator means, adapted for actuation from external to the patient by a direct manual thrust, said releaser means being in the fluid path between said actuator neans and said stiffener means, and serving, when actuated, to return fluid from said stiffener means to said actuator means through a substantially radial fluid flow port of said releaser means, thereby depressurizing the chamber of said stiffener means from said first pressure to a lower second pressure, causing said stiffener means to become flaccid; the outlet of said actuator means and the fluid flow port of said releaser being connected together with a substantially 90° displacement angle therebetween and by means of flexible tubing in such manner that the actuator means and the releaser means can be implanted in substantial contact with one another, while allowing substantial relative movement therebetween.

* * * * *